United States Patent [19]

Schiff

[11] 4,287,892
[45] Sep. 8, 1981

[54] CANNULA FOR INTRA-AORTIC BALLOON DEVICES AND THE LIKE

[76] Inventor: Peter Schiff, Box 354 Rte. 7, Cookeville, Tenn. 38501

[21] Appl. No.: 126,452

[22] Filed: Mar. 3, 1980

[51] Int. Cl.³ ............................................. A61M 25/00
[52] U.S. Cl. ................................................ 128/349 B
[58] Field of Search ............... 128/348, 349 R, 349 B, 128/349 BV

[56] References Cited

U.S. PATENT DOCUMENTS

| | | | |
|---|---|---|---|
| 3,707,972 | 1/1973 | Villari et al. | 128/349 R |
| 3,923,065 | 12/1975 | Nozick | 128/348 |
| 4,016,871 | 4/1977 | Schiff | 128/1 D X |
| 4,122,858 | 10/1978 | Schiff | 128/348 |

Primary Examiner—Harland S. Skogquist
Attorney, Agent, or Firm—Weinstein & Sutton

[57] ABSTRACT

A cannula assembly for intra-aortic balloon devices and the like comprising a Y-connector having a tube secured thereto with an inner diameter which is constant or which increases in diameter at the proximal end. Said tube is of a laminated construction in which the inner tubular member has a low friction characteristic while the outer tubular member provides the supporting strength for the laminated tubular construction.

A positioning ring is permanently secured to the cannula a spaced distance from its distal end to limit the extent to which the cannula is inserted into an artery through the arterial wall. The proper length of the penetration into the artery is controlled by cutting off a portion of the distal end sufficient to prevent the cannula from being extended through the opposite arterial wall, for example. The ring is preferably a split ring to facilitate cutting of the cannula to remove the cannula from the balloon and balloon catheter.

The Y-connector cooperates with a balloon catheter adapter to permit proper positioning of the intra-aortic balloon within the aortic arch while preventing the undesirable egress of any body fluids. A stretchable silicone sleeve provides the seal between the cooperating branch of the Y-shaped connector and the aforesaid catheter adapter.

An inlet branch of the Y-shaped connector may be coupled to a source of oxygenated blood obtained from a heart-lung machine, for delivery to the arterial line. A venting barb is provided for venting air developed within the cannula assembly to the atmosphere. The venting barb is sealed by clamping a stretchable tube mounted upon the venting barb with a releasable type clamp.

29 Claims, 12 Drawing Figures

CANNULA FOR INTRA-AORTIC BALLOON DEVICES AND THE LIKE

BACKGROUND OF THE INVENTION

Intra-aortic balloon assemblies are presently employed in the treatment of heart patients to augment the pumping action of a weak heart. Typically, the intra-aortic balloon assembly is inserted into the femoral artery and is inflated during diastole and deflated during systole to decrease left ventricular pressure and hence provide supportive activity for the heart. Immediately after leftventricular ejection, the intra-aortic balloon is inflated to raise diastolic pressures and to increase coronary perfusion, thereby mechanically assisting and augmenting the pumping action of the heart to remove the full burden of pumpingfrom a weakened or damaged heart.

The intra-aortic balloon is conventionally placed in position by making an incision in the patient's artery and suturing a graft to the artery. The balloon is inserted through the graft and is maneuveredto the desired position. The graft is tied snugly about the catheter in an effort to control bleeding.

An adapter is employed in conjunction with the aforesaid graft to permit unimpeded movement of the balloon to the precise location for optimum pumping while at the same time preventing the egress of any body fluids or blood from the slidingconnection made between the adapter and the graft. This technique is taught for example in FIG. 1 of applicant's issued U.S. Pat. No. 4,122,858.

In applications wherein it is desired to monitor blood pressure and in fact to cleanse and oxygenate the patient's blood, it is possible to employ a Y-shaped adapter of the type disclosed in the aforementioned U.S. Pat. No. 4,122,858. The Y-shaped adapter of U.S. Pat. No. 4,122,858 has an elongated preferably straight hollow main portionwith a pair of hollow branch portions branching off at an angle from the straight hollow portion. The hollow interior of the branch portions communicate with the hollow interior of said hollowmain portion. The main portion of the Y-shaped cannula is inserted into the aorta and is connected thereto. The Y-shaped cannula is formed of a flexible material. The balloon and balloon catheter are inserted into one of the branch portions and the common portion of the Y-shaped cannula. The branch portion receiving the balloon catheter is pinched or otherwise squeezed tight about the balloon catheter to prevent the escape of body fluids while the balloon adapter is moved along the catheter in order to be secured in position just inside the free end of the cannula arm portion receiving the balloon catheter. A coupling is connected to the free end of the remaining branch portion of the Y-cannula for connecting heart-lung apparatus to the Y-shaped cannula to provide the patient with oxygenated blood, for example, through a bypass technique.

In the Y-shaped adapter of aforementioned U.S. Pat. No. 4,122,858, theintra-aortic balloon is inserted directly into blood-flow portion of the cannula rather than in the blind end formed by one of the Y branches. The cannula is constructed to have a constant inner diameter since it has been found that it is not possible to push the intra-aortic balloon from a large diameter tube into a smaller diameter tube. It is possible to push an intra-aortic balloon through members either having a constant inner diameter or from one member having a first inner diameter into the next member having a larger inner diameter. In opposition to this, in order to keepblood turbulence to a minimum, in present perfursion cannulas, it is preferred that the catheter have a large diameter at the end adjacent to the heart-lung machine and taper gradually to a smaller diameter at the end inserted in the aorta.

BRIEF DESCRIPTION OF THE INVENTION

The present inventionovercomes the above-mentioned shortcomings of conventional cannulas and in addition provides the desirable characteristics described above through the use of a Y-shaped adapter preferably provided with barbed connector tube portions for respective coupling to: the portion of the cannula receiving the intra-aortic balloon and balloon catheter; the tubular member coupling the Y-connector to a heart-lung machine; and for connection to a silicone sleeve for positioning and sealing the intra-aortic balloon adapter thereto.

The semi-flexible portion of the Y-shaped adapter is of a laminated construction in which the internal tubular member is formed of a material having a low coefficient of friction while an outer tubular member having a greater wall thickness than the internal tubular member is provided for its inherent supporting strength.

A ring shaped member is secured about the exterior of the semi-flexible cannula a spaced distance inwardly from its distal end to serve as a stop means for preventing the cannula from being inserted into the arterial wall beyond a desirable distance. Appropriate adjustment of the length of the distal end of the cannula extendingbeyond the aforesaid stop ring is accomodated by trimming an appropriate amount of the distal end of said semi-flexible cannula.

The Y-shaped adapter is arranged so that the common arm and one branch thereof are axially aligned while the remaining branch of the Y-shaped adapter is offset at an angle relative to said common axis. The balloon catheter for the intra-aortic balloon extends through the axially aligned common arm and said one branch to prevent the formation of any bendsor elbows in the balloon catheter from impeding the insertion or movement of the catheter or balloon along the cannula or from impeding the pumping operation of the intra-aortic balloon.

The useof a semi-flexible cannula portion whose unstretched inner diameter (I.D.) is substantiallyidentical to the I.D. of the Y-shaped adapter or "Y-shaped end" makes it possible to keep blood turbulence to a minimum and yet provides an inner diameter which is uniform over the length of the cannula to facilitate accurate positioning of the intra-aortic balloon and its catheter.

In a preferred embodiment, the Y-shaped adapter is configured to receive the balloon catheter adapter within the interior bore. The catheter adapter is locked in place within the Y-shaped adapter by means of: a resilient O-ring which is wedged between a cooperating first shoulder provided in the interior bore of the Y-shaped adapter and a second shoulder provided in a resilientsleeve mounted upon one end of the catheter adapter; and a locking pin inserted through openings in the Y-shaped adapter to prevent movement of the catheter adapter relative to the Y-shaped adapter and to maintain a liquid-tight seal created by the cooperating compression of the resilient O-ring between said first and second shoulders in the Y-shaped adapter and the catheter adapter. The Y-shaped adapter may be totally removed from the balloon and balloon cathether by removing the locking pin, sliding the catheter adapter out of the Y-shaped adapter and thereafter removing the O-ring. The outer diameter of the catheter adapter is less than the inner diameter of the bore in the Y-shaped adapter common end and in the cannula tube to permit the catheter adapter to pass therethrough when the cannula tube and Y-shaped adapter are being removed. Alternatively, the cannula tube may be cut in half and then removed.

The Y-shaped adapter may be provided with a venting branch to vent air bubbles developed in the cannula assembly to the atmosphere. A resilient tube stretched over the opening of the venting branch may thereafter be sealed by a suitable clamp to maintain the desired liquid-tight seal.

BRIEF DESCRIPTION OF THE FIGURES AND OBJECTS OF THE INVENTION

It is therefore one object of the presentinvention to provide a novel cannula of simplified design which facilitates insertion, placement and proper operation of intra-aortic balloons.

Still another object of the present invention is to provide a novel Y-shaped cannula assembly for use with intra-aortic balloons and the like having an interior configuration provided to facilitate slidable movement of the intra-aortic balloon without impeding accurate positioning of the intra-aortic balloon.

Still another object of the presentinvention is to provide a novel Y-shaped cannula assembly of the type described hereinabove wherein a semi-flexible cannula portion of laminated construction is employed for facilitating movementand placement of the intra-aortic balloon and its balloon catheter within the cannula without impeding the positioning operation.

Still another object of the present invention is to provide a novel Y-shaped cannula assembly employing a semi-flexible cannula portion of multiple tube construction wherein the internal tube is formed of a material which facilitates sliding movement of the intra-aortic balloon along the interior thereof while the external tube provides adequate supporting strength therefor.

Still another object of the presentinvention is to provide a novel Y-shaped cannula assembly having a semi-flexible cannula portion provided with a stop ring extending about the exterior of said semi-flexible cannula portion a spaced distance from its distal end to limit the distance which the semi-flexible cannula portion of the cannula assembly may penetrate into the artery through the arterial wall.

Another object of the present invention is to provide a Y-shaped cannula assembly for use with a balloon catheter and which is designed to cooperate with a balloon adapter to provide a liquid-tight seal with the aid of a resilient O-ring and a locking member wherein the Y-shaped cannula may be completely removed from a balloon catheter and balloon adapter by removal of the locking member and O-ring to permit the balloon adapter to freely pass through the Y-shaped cannula assembly in the absence of the O-ring.

Still another object of the presentinvention is to provide a Y-adapter for use with a balloon catheter and cooperating with a balloon catheter adapter to create a lquid-tight seal by means of compressing a resilient O-ring and a resilient sleeve positioned between the Y-adapter and the balloon catheter adapter, said sleeve further providing a sliding liquid-tight seal between the balloon catheter adapter and the balloon catheter.

Another object of the present invention is to provide a cannula assembly having a Y-adapter for use with a balloon catheter and having a venting barb for selectively venting the interior of the cannula assembly to the atmosphere.

The above as well as other objects of the present invention will become apparent while reading the accompanying description and drawings in which:

DETAILED DESCRIPTION OF THE INVENTION

Figure 1:
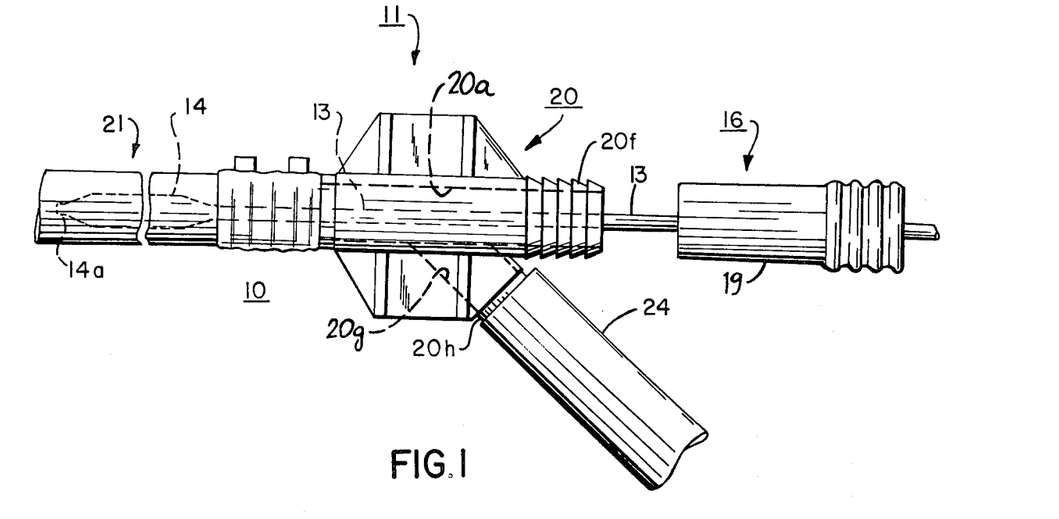
FIG. 1 shows a simplified schematic-type plan view of a cannula assembly having a Y-shaped adapter for use with intra-aortic balloons and the like and embodying the principles of the present invention.
Figure 1A:
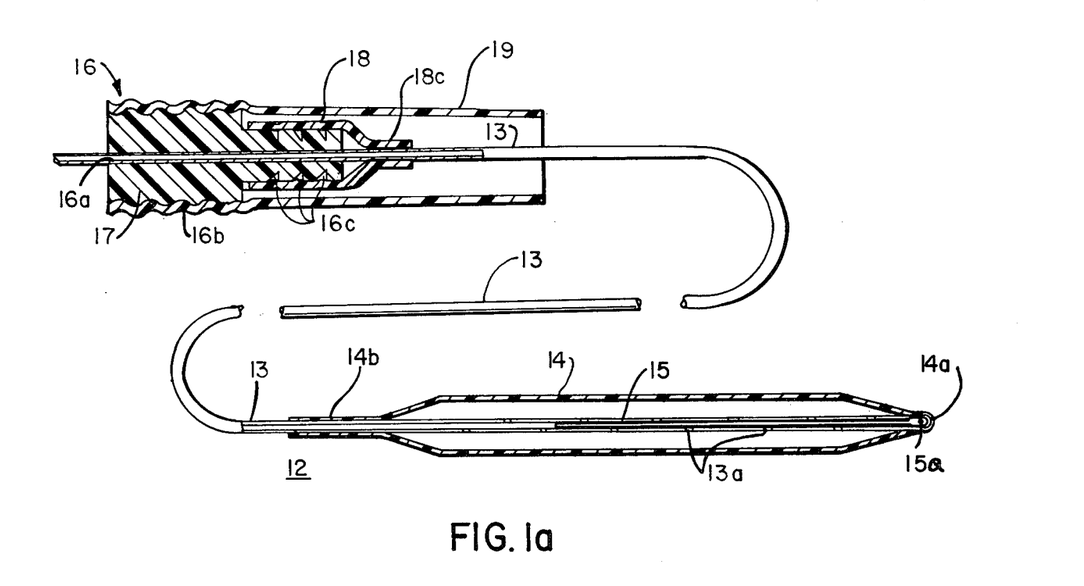
FIG. 1a shows a sectional view of the balloon and catheter adapter of FIG. 1.

FIG. 1 shows an assembly 10 comprised of a Y-shaped cannula assembly 11 for use with an intra-aortic balloon and balloon catheter assembly 12, shown in FIG. 1a.

Figure 2:
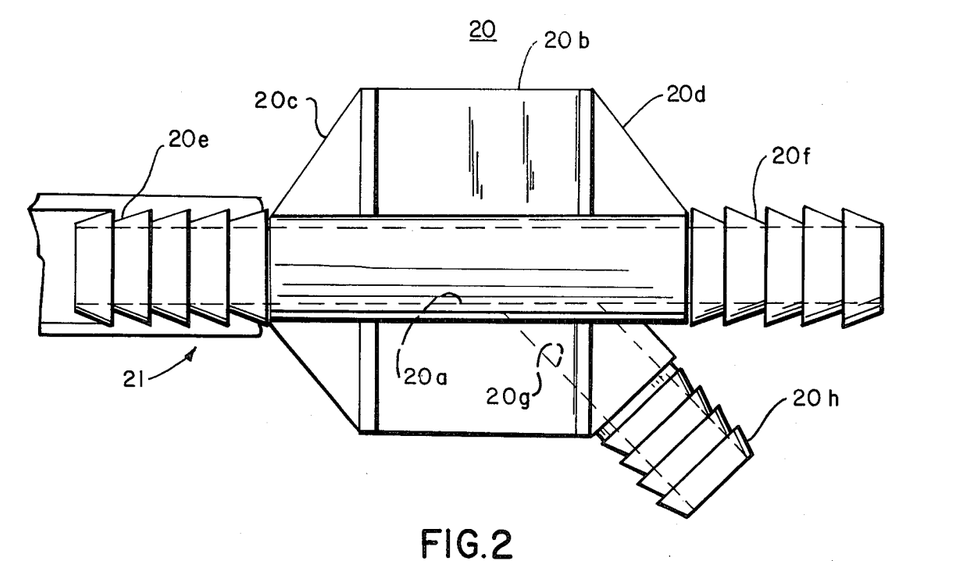
FIG. 2 shows a detailed plan view of the Y-connector of the cannula assembly of FIG. 1.

The intra-aortic balloon 14 is described, for example, in detail in U.S. Pat. No. 4,175,264. As shown in FIG. 2, the intra-aortic balloon is comprised of a balloon portion 82 mounted upon a catheter 81 for rhythmic inflation and deflation in synchronism with the patient's heartbeat for the purpose of assisting in the pumping of blood to reduce the work load imposed upon the heart which otherwise has the total responsibility for pumping blood through the patient's body.

FIG. 1a of the present application shows the intra-aortic balloon 14 and balloon catheter assembly 12 comprised of a balloon catheter 13 having a seamless balloon 14 integral therewith. The distal end 14a of the balloon encircles and is air-tightly sealed to a front tip conventionally provided with a metallic insert 15a visible in an X-ray and/or fluroscope for use in accurately locating the front tip 15a of the balloon within the descending portion of the aorta.

Catheter 13 is provided with a plurality of openings 13a arranged along the portion of the catheter 13 which is enclosed by balloon 14. The opposite end 14b of balloon 14 is air-tightly sealed to the adjacent portion of the balloon catheter 13 spaced inwardly from tip 15a. An elongated rod-shaped member 15 extends through a portion of the length of said catheter 13 to regulate the manner of inflation of the intra-aortic balloon 14.

A balloon catheter 16 is slidably mounted upon balloon catheter 13 and is comprised of a body member 16 and a first stretchable silicone sleeve 18. An axial bore 16a extends through body member 16. The V-shaped grooves or barbs 16b and 16c are arranged about the larger and smaller diameter portions respectively of the body member 16. The V-shaped grooves or barbs 16c serve to lock the stretched portion of silicone sleeve 18 gripping the barbs 16c. Sleeve 18 is formed of a resilient stretchable silicone. The right-hand portion of sleeve 18 is contracted, relative to its left-hand portion, to its normally unstretched condition in order to form a liquid-tight sliding seal about the balloon catheter 13.

A second stretchable silicone sleeve 19 of a larger diameter than sleeve 18 is stretched about the larger diameter portion of body member 16 in the manner shown to firmly grip the grooves 16b and envelops the smaller diameter portion 16c as well as the smaller diameter silicone sleeve 18.

The right-hand portion of larger diameter silicone sleeve 19 is adapted to be stretched over a barbed projection 20f (see FIGS. 1 and 2) extending from the Y-shaped cannula adapter member 20, as will be more fully described, to create a good liquid-tight seal therebetween, which arrangement allows the balloon 14 and hence the balloon catheter 13 to be slidably moved relative to the Y-shaped adapter 20 to be properly positioned within the body of the patient (not shown) while at the same time preventing the escape of body fluids from the patient.

Figure 3:
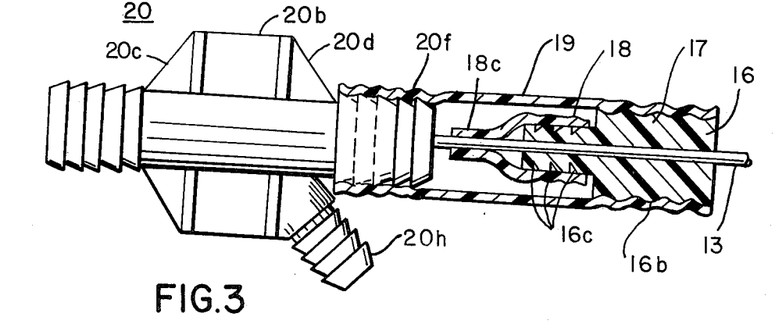
FIG. 3 shows a detailed view of the manner in which the Y-shaped cannula assembly cooperates with the balloon catheter adapter assembly.

The Y-shaped adapter assembly 11 is shown best in FIGS. 1, 2 and 3 and is comprised of a Y-connector 20 formed of a transparent material and having a central bore 20a extending over the axial length of the connector 20. The main body portion 20b is generally cylindrical in shape and has opposite conical shaped tapering sides 20c and 20d, each terminating in a barbed connector section 20e and 20f respectively, said central opening 20a extending through both of said connecting projections 20e and 20f. A bore 20g extends at an angle to and communicates with bore 20a. Bore 20g extends through barbed connector projection 20h. As shown best in FIG. 2, the bore 20a is of a constant diameter over its entire length.

Figures 4, 5A:
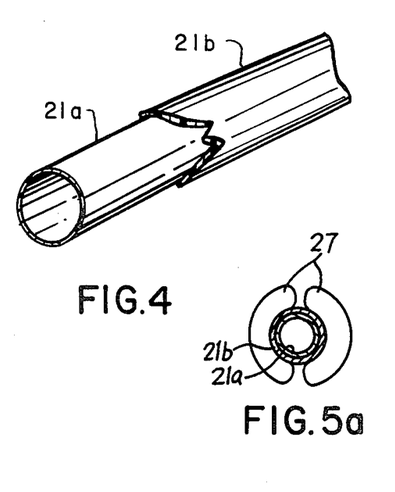
FIG. 4 shows a detailed perspective view of the semi-flexible portion of the cannular assembly, partially sectionalized.
FIG. 5a shows an end view of the cannula of FIG. 5 showing the split ring of FIG. 5 in greater detail.

The cannula assembly 11 is further comprised of a semi-flexible tubular portion 21 of laminated construction and, as shown best in FIG. 4, is comprised of an internal sleeve 21a and an external sleeve 21b. Sleeve 21a is quite thin and is formed of a plastic material having a low coefficient of friction. In one preferred embodiment, the sleeve 21a is formed of a thin polyethylene sheet having a wall thickness of the order of 0.05 to 0.030 inches and preferably in the range from 0.010 to 0.020 inches. The outer sleeve 21b is preferably formed of a polyurethane sheet having a wall thickness of the order of 0.030 to 0.050 inches and preferably in the range from 0.035 to 0.045 inches. The inner diameter of inner sleeve 21a is preferably equal to the innter diameter of bore 20a. The right-hand end of the laminated tubular structure 21 is stretched over the barbed coupling 20e to form a liquid-tight seal therebetween. As an alternative, the proximal end 21e of the semi-flexible cannula tube 21 may be of an increasing diameter while the remaining part of tube 21 is of a constant diameter. This arrangement facilitates mountingof tube 21 upon coupling projection 20e and assures that the I.D. of tube 21 at its narrow portion is at least equal to the I.D. of bore 20a.

FIG. 1 shows the intra-aortic balloon 14 positioned within the cannula tube 21 coupled to Y-shaped cannula assembly 11. The intra-aortic balloon 14 is positioned toward the distal end thereof and its catheter 13 extends rearwardly through laminated tubular cannula member 21 and bore 20a of Y-connector 20 and outwardly through coupling projection 20f. The stretchable sleeve 19 is shown in FIG. 1, which shows the catheter adapter assembly 16 displaced from Y-connector 20 while FIG. 3 shows the catheter adapter assembly 16 positioned adjacent to projection 20f and shows the left-hand end of sleeve 19 stretched over and forming a liquid-tight seal with barbed coupler 20f.

In FIG. 1, the free end of a hollow flexible tube 24 is stretched over upon and forms a liquid-tight seal with barbed coupling projection 20h. Tube 24 couples the Y-shaped cannula assembly 11 to a heart-lung machine (not shown) to provide oxygenated blood to the patient, typically through a bypass apparatus such as, for example, the bypass pump described in applicant's aforementioned U.S. Pat. No. 4,122,858.

The Y-shaped cannula assembly 11 and balloon apparatus 12 operates in the following manner:

Although not shown for purposes of simplicity, it should be understood that the cannula and balloon assembly 10 of FIG. 1 is preferably packaged within a sterile enclosure such as, for example, a sealed plastic bag of suitable size.

Figure 5:
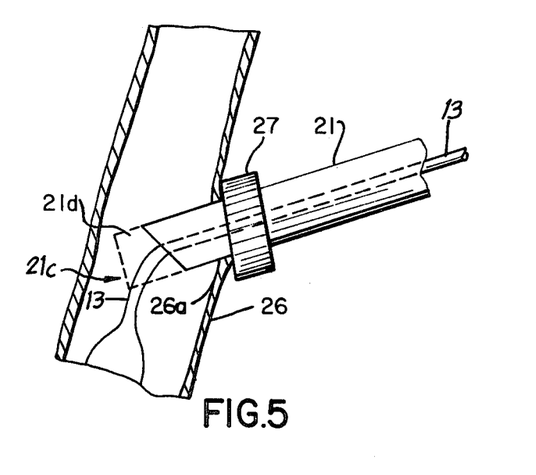
FIG. 5 shows a detailed view of the cannula stop ring and the manner in which the ring operates to limit the penetration distance of the cannula into an artery.

An incision 26a is made in the arterial wall 26, as shown in FIGS. 5 and 5a. The laminated cannula tube 21 is provided with a small ring-shaped member 27 which, for example, is preferably permanently secured to the exterior sleeve 21b by a suitable cement or a solvent. The distal end 21c of the laminated cannula tube21 is inserted into the artery at an angle of less than 90° through the incision 26a to allow the balloon 14 to enter into the aorta more easily. In order to avoid pushing the cannula tube 21 too far into the artery, the surgeon makes a determination of how far the cannula should penetrate in the aorta or other artery and simply cuts off the excess 21d of the distal portion of laminated cannula tube 21. The depth of penetration of the tip portion is thus limited by virtue of the fact that the ring-shaped stop member 27 abuts against the exterior of the arterial wall to prevent any further penetration. A suitable length of cannula tube is provided beyond the ring-shaped member 27 to accommodate the dimensional range typically encountered, by positioning the stop member 27 several inches inwardly from the distal end of tube 21. As can be seen from FIG. 5a, stop member 27 is a split-ring formed of ring halves 27a and 27b to facilitate splitting, i.e. cutting, of cannula 21.

In FIG. 1, the tube 24 is stretched over the barbed coupling projection 20h and the stretchable silicone sleeve 19 is pushed over the barbed coupling projection 20f. The balloon catheter 13 may then be pushed to the left (relative to FIG. 1) to cause the intra-aortic balloon 14 to emerge from the distal end of laminated cannula tube 21 and to enter into the artery through the opening 26a in arterial wall 26. The low coefficient of sliding friction of inner sleeve 21a facilitates substantially unimpeded movement of the intra-aortic balloon 14 and balloon catheter 13 relative to the Y-shaped adapter 20 and tube 21 to permit rapid and precise positioning of the intra-aortic balloon 14. Oxygenated blood from the heart-lung machine enters through arterial tube 24 and barb 20g. The outer diameter of balloon catheter 13 is often less than the inner diameter of bore 20a to facilitate the flow of blood in the hollow annular region defined by their respective surfaces.

The liquid-tight seal formed between tube 24 and barbed projection 20h as well as the liquid-tight seal formed between barbed projection 20f and stretchable sleeve 19 prevents the loss of any blood. A sliding liquid-tight seal is formed between stretchable sleeve 18 and balloon catheter 13 to prevent the egress of blood or other body fluids through bore 16a in adapter 16. By extending the balloon catheter 13 in a straight-line fashion through bore 20a the formation of any bends or creases in the catheter 13 is prevented, thereby further facilitating movement of the intra-aortic balloon 14 and balloon catheter 13 during both insertion and removal of the intra-aortic balloon 14 from the operative location. In certain applications the balloon 14 may be inserted into cannula 21 for elective initiation later or even after bypass has been initiated.

FIGS. 6, 7, 7a, and 8 and 9 show alternative embodiments 30 of the invention which are comprised of a Y-adapter 31 having an axially aligned bore 31a extending through forward projection 32 and branch 33. Branch 34 is offset at an angle and is provided with bore 34a communicating with bore 31a. An auxiliary barb 35 has a bore 35a communicating with bore 31a.

The rearward portion 31b of bore 31a is of an enlarged diameter relative to forward portion 31a. A shoulder 31c joins bore portions 31a and 31b. A pair of openings 36a and 36b extend through branch 33, said openings extending in a direction perpendicular to the plane of FIG. 6.

Figure 8:
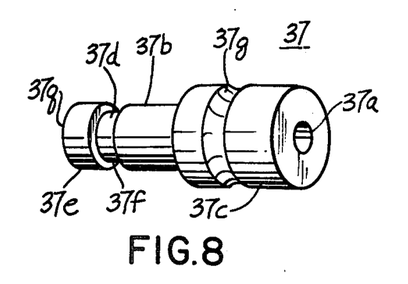
FIG. 8 is a perspective view of the catheter adapter of FIGS. 6 and 7.

The enlarged diameter bore portion 31b accommodates adapter 37 having an axially aligned bore 37a for slidably receiving balloon catheter 13 as shown in FIG. 8. Adapter 37 has a small diameter portion 37b and a large diameter portion 37c. Small diameter portion 37b is provided with a shallow recess 37d defining a tip 37e having a shoulder 37f spaced inwardly from the free end 37g of tip 37e. The enlarged diameter portion 37c is provided with recess 37g for seating a tie member wrapped about a graft encircling adapter 37, as will be more fully described.

Figures 6, 7:
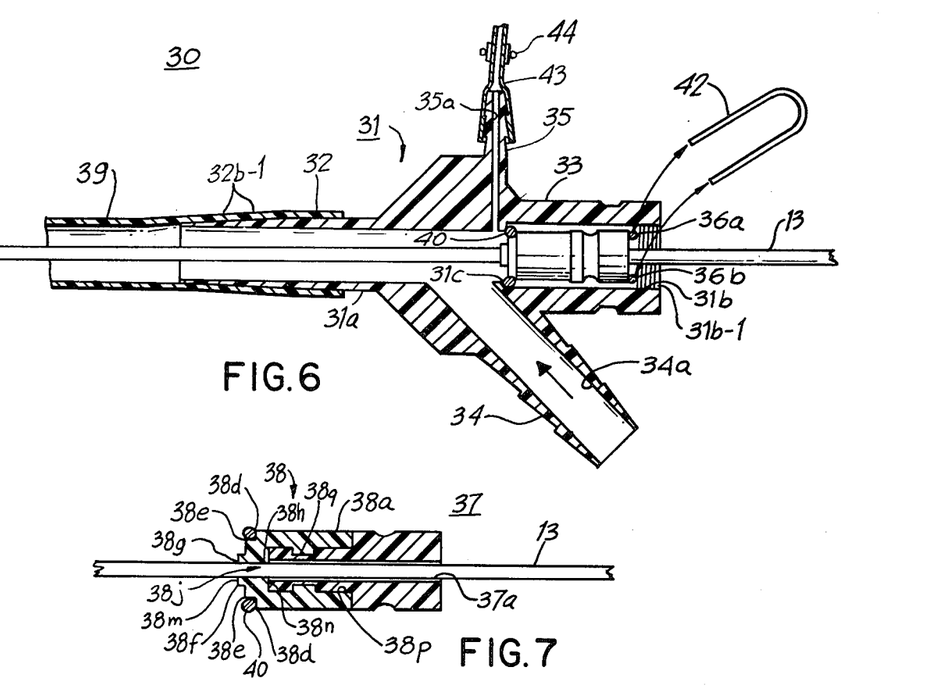
FIG. 6 is a sectional view of an alternative embodiment of the present invention.
FIG. 7 is a sectional view of the catheter adapter and cooperating sleeve shown in FIG. 6.
Figure 7A:
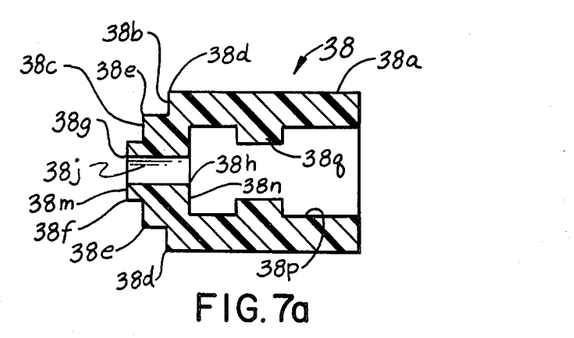
FIG. 7a shows an enlarged view of the sleeve of FIG.7.

A sleeve 38 is force-fitted over small diameter portion 37b of adapter 37 in the manner shown in FIG. 7. Sleeve 38 is a molded silicone member having a major surface portion 38a. The forward end of sleeve 38 is provided with first and second annular surface portions 38b and 38c of successively reduced diameters defining sharp edges 38d, 38e and 38f. There is also a pair of sharply defined circular-shaped edges 38g and 38h between the opening 38j provided in the forward end of sleeve 38 and the forward surface 38m and interior surface 38n.

A projection 38q is integrally molded into the interior surface 38p of sleeve 38. The width and length of projection 38q are less than the width and depth of recess 37d in order to snugly fit into recess 37 when placed upon the left-hand end of adapter 38 as shown in FIG. 7. Alternatively, the sleeve 38 may be secured to adapter 37 by a suitable cement deposited in recess 37d.

The operation of the embodiment shown in FIGS. 6-8 is as follows:

A cannula tube 39 has its right-hand end stretched over the forward projection 32 which has a tapered exterior surface 32b provided with barbs 32b-1. Tube 39 is inserted into the arterial wall in a manner similar to that described above in connection with the embodiment of FIGS. 1-5.

The balloon 14 and balloon catheter 13 (see FIG. 1a) are preloaded prior to use by the manufacturer in the embodiment of FIGS. 6, 7 and 8, whereby the balloon 14, catheter adapter 37, catheter 13 and O-ring 40 occupy the positions shown in FIG. 6. O-ring 40 is wedged against shoulder 31c in the manner shown. U-shaped locking pin 42 mounted in openings 36a, 36b, holds adapter 37 in the position shown in FIG. 6 with O-ring 40 wedged between sleeve 38 and shoulder 31c. The liquid-tight seal between O-ring 40 and shoulder 31c prevent body fluids from flowing out of Y-adapter 31.

Auxiliary barb 35 allows any air bubbles developed within cannula tube 39 and/or Y-shaped adapter 31 to be vented to the atmosphere through the bore 35a in barb 35 and through hollow silicone tube 43, whose lower end is stretched over bar 35. Barb 35 is sealed by means of a releasable clamp 44 shown in schematic as clamping tube 43, said clamp preferably being of the type commonly referred to as a "bulldog" clamp. If desired, however, any other suitable clamp may be employed for selectively sealing the venting opening provided by barb 35.

The branch 34 of Y-shaped adapter 31 may be employed to couple a blood-oxygenator and/or bypass machine to cannula 31 in the same manner as was described in connection with the embodiment 10 of FIGS. 1-5.

In the event that it is desired to remove the bypass and/or oxygenator equipment from the patient while maintaining the balloon 14 and balloon catheter 13 for post-operative support, the Y-shaped adapter 31 and cannula 39 may be completely removed by removing the locking pin 42 from its locking position in openings 36a-36b. Catheter adapter 37 is then slidably moved rearwardly along balloon catheter 13 until it is completely withdrawn from Y-shaped adapter 36. O-ring 40 is then removed from its locking position at the forward end of silicone sleeve 38 preferably by cutting the O-ring. Tube 39 may be cut in half to facilitate its removal. Split ring 27 simplifies the cutting of tube 39. Y-shaped adapter 31 and cannula tube 39 may then be moved towards the right along catheter 13 (relative to FIG. 6). Sufficient clearance exists between the inner diameters of both bores 31a and 31b and the inner diameter of tube 39 and the outer diameter of sleeve 38 and adapter 37 to allow the catheter adapter 37 and sleeve 38 to pass completely through bores 31c and 31b and tube 39 (in the absence of O-ring 40) as Y-shaped cannula 31 and tube 39 are moved to the right relative to balloon catheter 13 and catheter adapter 37.

Since the balloon 14 comes preloaded in the embodiment of FIG. 6, the plastic Y-adapter 31 inside diameter 31a may be larger (and always large enough to pass the catheter adapter 37) than the inside diameter of the cannula 39. If the cannula 39 (flexible part) is too small to pass the diameter of catheter 13, then the tube 39 is preferably split by cutting to facilitate removal of the balloon 14 when the balloon 14 is to be left in the patient post-operatively.

Adapter 37 is then inserted into one end of a dacron or other suitable graft, shown for example, in FIG. 1 of above-mentioned U.S. Pat. No. 4,122,858, which is sewn into the artery. A thread is tied about the graft in the region of groove 37g to provide a blood-tight seal to prevent loss of body fluids while maintaining the integrity of the balloon and balloon catheter assembly during the post-operative phase of patient care.

Figure 9:
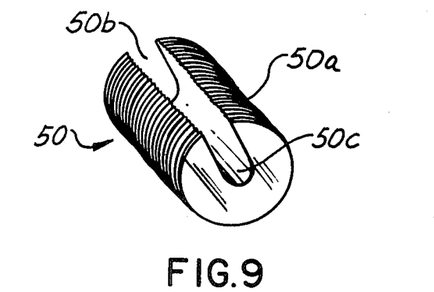
FIG. 9 is a perspective view of an alternative locking-member which may be substituted for the locking pin of FIG. 6.

It will be understood that the embodiments described above are merely exemplary and the person skilled in the art may make many variations and modifications without departing from the spirit and scope of the invention. All such modifications and variations are intended to be included within the scope of the invention as defined in the appended claims. For example, the locking pin 42 may be replaced by the cylindrical-shaped locking member 50 having a threaded exterior 50a as shown in FIG. 9. The rear portion 31b of bore 31a is tapped at 31b-1 to receive and threadedly engage locking member 50. Locking member 50 has a slot 50b whose base portion 50c is axially aligned with the longitudinal axis of bore 31a so as to be aligned with and receive balloon catheter 13 therealong. Locking member 50 is threadedly inserted into bore 31a to compress O-ring 40 between catheter adapter 37 and shoulder 31c. To remove Y-adapter 31 from the balloon 14 and balloon catheter 13, locking member 50 is unscrewed from bore 31a. Catheter adapter 37 is moved out of bore 31a. O-ring 40 is removed and Y-adapter 31 and sleeve 38 may be freely slipped over catheter adapter 37.

What is claimed is:

1. A cannula assembly for use with intra-aortic balloons and the like comprising a rigid Y-shaped connector having a first bore extending therethrough and a branching bore communicating with said first bore and extending at an angle thereto; said first bore having first and second ends; said fitting being provided with first, second and third coupling projections; said first bore extending through said first and second coupling projections and said second bore extending through said third coupling projections; and
    a cannula tube having a first end thereof mounted upon said first coupling projection to form a liquid-tight seal therebetween; the inner diameter of said cannula tube and said first bore being substantially equal.

2. The cannula assembly of claim 1, wherein said cannula tube is comprised of first and second elongated sleeves, said first sleeve being formed of a material having a low coefficient of sliding friction; and
    said second sleeve being substantially equal in length to said first sleeve and surrounding said first sleeve.

3. The cannula assembly of claim 2, wherein the thickness of said first sleeve is less than the thickness of said second sleeve.

4. The cannula assembly of claim 3, wherein said first sleeve if formed of polyethylene.

5. The cannula assembly of claims 3 or 4, wherein said second sleeve is formed of polyurethane.

6. The cannula assembly of claims 3 or 4, wherein said first sleeve has a wall thickness in a range from 0.0050 to 0.030 inches.

7. The cannula assembly of claims 3 or 4, wherein said second sleeve has a thickness of the order of 0.030 to 0.050 inches.

8. The cannula assembly of claim 1, further comprising an intra-aortic balloon assembly extending through said Y-shaped connector and comprising an intra-aortic balloon adapted to be extended through said cannula tube and a balloon catheter coupled to said intra-aortic balloon and extending through said cannula tube and said first bore.

9. The cannula assembly of claim 8, further comprising adapter means slidably mounted upon said balloon catheter and positioned adjacent to said second coupling projection and adapted to provide a liquid-tight sliding seal between said balloon catheter and said adapter means; and
    stretchable sleeve means for providing a liquid-tight seal between said second coupling projection and said adapter means.

10. The cannula assembly of claim 1, further comprising tube means having a first end positioned over said third coupling projection and adapted to couple said second bore to a source of oxygenated blood.

11. The cannula assembly of claim 1, wherein said Y-connector is formed of a rigid clear plastic material.

12. The cannula assembly of claim 11, wherein said Y-shaped connector is formed of a polycarbonate material.

13. The cannula assembly of claim 1, further comprising a ring-shaped member secured to the outer wall of said cannula tube a spaced distance inwardly from the free end of said tube remote from said Y-connector and adapted to serve as a stop means to control the depth of penetration of said cannula tube into an arterial wall.

14. The cannula assembly of claim 13 wherein said ring-shaped member is formed of a pair of ring halves forming a split ring, the ends of said ring halves being displaced from one another.

15. The cannula assembly of claim 9, wherein said adapter means is comprised of an annular-shaped body having an elongated bore extending therethrough and adapted to slidably receive said balloon catheter; and
    a second resilient stretchable plastic sleeve positioned about one end of said body and about said balloon catheter so as to embrace and form a sliding fluid-tight seal about said balloon catheter whereby said body is adapted to be slidably positioned at any point along said tubular member while maintaining the integrity of the sliding seal between said second sleeve and said balloon catheter.

16. The cannula assembly of claim 15, wherein said body is further comprised of a portion having a larger diameter than said first portion about which said first stretchable sleeve is secured and being adapted to receive said first liquid-tight sleeve means.

17. The cannula assembly of claim 1, wherein the coupling projections of said Y-connector have barbed exterior surfaces which are adapted to cooperate with the stretchable sleeves mounted thereon to assure the formation of a good liquid-tight seal therebetween.

18. A cannula for use with intra-aortic balloon assemblies and the like comprising:
    a housing having a bore extending therethrough for receiving a balloon catheter and provided with a shoulder intermediate the ends of said bore;
    an adapter having a bore for slidably receiving a balloon catheter being positioned within said bore;
    resilient means at one end of said adapter for engaging said shoulder to provide a liquid-tight seal between said housing bore and said adapter; and
    locking means engaging said housing and said adapter for retaining said adapter and resilient means in the liquid-tight sealing condition.

19. The cannula of claim 18 wherein the inner diameter of said bore at its narrowest point is greater than the outer diameter of said adapter to permit the adapter to be passed completely through said bore when said resilient means is removed.

20. The cannulaof claim 18 wherein said resilient means comprises a resilient O-ring.

21. The cannula of claim 18 further comprising a resilient sleeve placed over one end of said adapter and having an opening surrounding and forming a sliding liquid-tight seal about said balloon catheter.

22. The cannula of claim 21 wherein a first surface of said sleeve surrounding said opening and a second surface comprising the surface of said opening meet to form a sharp edge therebetween to enhance the liquid-tight sliding seal.

23. The cannula of claim 22 wherein said first surface is substantially perpendicular to the longitudinal axis of said opening.

24. The cannula of claim 18 wherein said bore has a first large diameter portion and a secondsmaller diameter portion, said shoulder being positioned between said first and second portions; the diameter of said first portion being greater than the outer diameter of said adapter.

25. The cannula of claim 1 further comprising a venting projection on said connector having an opening communicating with one of said bores for venting air in said bores to the atmosphere; and sealing means for releasably sealing said venting projection.

26. The cannula of claim 25 wherein said sealing means comprises a hollow sleeve having one end mounted over said projection; and clamping means for releasably sealing said sleeve.

27. The cannula of claim 18 wherein said housing is provided with openings perpendicular to the longitudinal axis of said housing bore for receiving said locking means for retaining said resilient means and said adapter between said shoulder and said locking means.

28. The cannula of claim 18 wherein said locking means comprises a threaded member having a slot for slidably, removably receiving said catheter; and said housing bore having a tappedportion for threadedly engaging said threaded member to position said threaded member to be urged against said adapter to compress said resilient means between said adapter and said shoulder.

29. The cannula of claim 18 wherein said locking means comprises a U-shaped locking pin having arms extending through openings in said housing and engaging and urging said adapter toward said shoulder.

* * * * *

UNITED STATES PATENT AND TRADEMARK OFFICE
CERTIFICATE OF CORRECTION

PATENT NO. : 4,287,892
DATED : September 8, 1981
INVENTOR(S) : Peter Schiff

It is certified that error appears in the above—identified patent and that said Letters Patent is hereby corrected as shown below:

In Column 1:

line 13, change "leftventricular" to --left ventricular--.

line 17, change "pumpingfrom" to --pumping from-- line 22, change "maneuveredto" to --maneuvered to-- line 29, change "slidingconnection" to --sliding connection-- line 39, change "portionwith" to --portion with-- line 42, change "hollowmain" to --hollow main-- line 60, change "theintra-aortic" to --the intra-aortic--

In Column 2:

line 3, change "keepblood" to --keep blood-- line 10, change "inventionovercomes" to --invention overcomes-- line 43, change "bendsor" to --bends or-- line 48, change "useof" to --use of-- line 49, change "substantiallyidentical" to --substantially identical--

UNITED STATES PATENT AND TRADEMARK OFFICE
CERTIFICATE OF CORRECTION

PATENT NO. : 4,287,892          Page 2 of 5
DATED      : September 8, 1981
INVENTOR(S) : Peter Schiff It is certified that error appears in the above—identified patent and that said Letters Patent is hereby corrected as shown below:

line 63, change "resilientsleeve" to --resilient sleeve--

In Column 3:

line 21, change "presentinvention" to --present invention-- line 32, change "presentinvention" to --present invention-- line 36, change "movementand" to --movement and-- line 46, change "presentinvention" to --present invention-- line 64, change "presentinvention" to --present invention-- line 67, change "lquid-tight" to --liquid-tight--

In Column 5:

line 19, change "handportion" to --hand portion-- line 57, change "plasticmaterial" to --plastic material-- line 66, change "innter" to --inner--

UNITED STATES PATENT AND TRADEMARK OFFICE
CERTIFICATE OF CORRECTION

PATENT NO. : 4,287,892  Page 3 of 5
DATED : September 8, 1981
INVENTOR(S) : Peter Schiff It is certified that error appears in the above—identified patent and that said Letters Patent is hereby corrected as shown below:

In Column 7:

line 10, change "theirrespective" to --their respective-- line 16, change "andballoon" to --and balloon--
lines 35-36, change "anen-larged" to --an enlarged-- line 39, change "directionperpendicular" to --direction perpendicular--

In Column 8:

line 30, change "ventingopening" to --venting opening-- line 47, change "siliconesleeve" to --silicone sleeve-- line 57, change "Y-shapedcannula" to --Y-shaped cannula-- line 60, change "Sincethe" to --Since the--

In Column 9:

line 10, change "merelyexemplary" to --merely exemplary-- line 14, change "inventionas" to --invention as--

UNITED STATES PATENT AND TRADEMARK OFFICE
CERTIFICATE OF CORRECTION

PATENT NO. : 4,287,892   Page 4 of 5
DATED : September 8, 1981
INVENTOR(S) : Peter Schiff It is certified that error appears in the above—identified patent and that said Letters Patent is hereby corrected as shown below:

line 27 change "50is" to --50 is-- and "bore31a" to --bore 31a-- line 37, change "firstbore" to --first bore-- line 39, change "firstand" to --first and-- and "couplingprojections" to --coupling projections-- line 42, change "cannulatube" to --cannula tube--

In Column 10:

line 28, change "serveas" to --serve as-- line 34, change "oneanother" to --one another-- line 52, change "havebarbed" to -have barbed-- line 55, change "formationof" to --formation of--

In Column 11:

line 6, change "cannulaof" to --cannula of-- line 21, change "secondsmaller" to --second smaller--

UNITED STATES PATENT AND TRADEMARK OFFICE
CERTIFICATE OF CORRECTION

PATENT NO. : 4,287,892  Page 5 of 5
DATED : September 8, 1981
INVENTOR(S) : Peter Schiff It is certified that error appears in the above—identified patent and that said Letters Patent is hereby corrected as shown below:

In Column 12:

line 18, change "tappedportion" to --tapped portion--.

Signed and Sealed this

Tenth Day of May 1983

[SEAL]

Attest:

Attesting Officer

GERALD J. MOSSINGHOFF

Commissioner of Patents and Trademarks